(12) United States Patent
Indraccolo et al.

(10) Patent No.: US 12,298,306 B2
(45) Date of Patent: May 13, 2025

(54) MARKER FOR IDENTIFYING PATIENTS WITH GLIOBASTOMA WHO RESPOND POSITIVELY TO THE DRUG REGORAFENIB

(71) Applicant: ISTITUTO ONCOLOGICO VENETO IOV-IRCCS, Padua (IT)

(72) Inventors: Stefano Indraccolo, Padua (IT); Gian Luca De Salvo, Padua (IT); Giuseppe Lombardi, Padua (IT)

(73) Assignee: Istituto Oncologico Veneto IOV-IRCCS, Padua (IT)

( * ) Notice: Subject to any disclaimer, the term of this patent is extended or adjusted under 35 U.S.C. 154(b) by 1085 days.

(21) Appl. No.: 16/980,122

(22) PCT Filed: Mar. 12, 2019

(86) PCT No.: PCT/IB2019/051991
§ 371 (c)(1),
(2) Date: Sep. 11, 2020

(87) PCT Pub. No.: WO2019/175763
PCT Pub. Date: Sep. 19, 2019

(65) Prior Publication Data
US 2021/0003573 A1   Jan. 7, 2021

(30) Foreign Application Priority Data
Mar. 12, 2018   (IT) .................. 102018000003449

(51) Int. Cl.
*A61K 31/44*   (2006.01)
*G01N 33/574*   (2006.01)

(52) U.S. Cl.
CPC ....... *G01N 33/57407* (2013.01); *A61K 31/44* (2013.01); *G01N 33/57496* (2013.01); *G01N 2333/9015* (2013.01); *G01N 2440/14* (2013.01)

(58) Field of Classification Search
None
See application file for complete search history.

(56) References Cited

U.S. PATENT DOCUMENTS

2013/0230511 A1   9/2013   Heymach et al.

FOREIGN PATENT DOCUMENTS

WO   WO 2008/089388   *   7/2008   ............. A61K 31/44

OTHER PUBLICATIONS

Saito et al (Neurochem Res 34:1945-1954, 2009) (Year: 2009).*
Rios et al (Cancer Res 73:2628-2638, 2013) (Year: 2013).*
Wilhelm et al (Int J Cancer 129:245-255, 2011) (Year: 2011).*
Rios et al. "AMPK Activation by Oncogenesis Is Required to Maintain Cancer Cell Proliferation in Astrocytic Tumors", Cancer Research, vol. 73, No. 8, Jan. 13, 2013, pp. 2628-2638, XP055520465.
Lombardi et al. "REGOMA: A randomized, multicenter, controlled open-label phase II clinical trial evaluating regorafenib activity in relapsed glioblastoma patients", Annal of Oncology Sep. 21, 2017, vol. 28, No. Supplement 5 XP009509077.
Wilhelm et al. "Regorafenib (BAY 73-4506): a new oral multikinase inhibitor of angiogenic, stromal and oncogenic receptor tyrosine kinases with potent preclinical antitumor activity." International Journal of Cancer 129, Dec. 17, 2010, pp. 245-255, XP055003945.
International Search Report for International Application No. PCT/IB2019/051991, mailed Jun. 12, 2019, 3 pages.

* cited by examiner

*Primary Examiner* — Craig D Ricci
(74) *Attorney, Agent, or Firm* — Armstrong Teasdale LLP

(57) ABSTRACT

The present invention relates to a marker for allowing the identification of patients with glioblastoma who respond positively to the drug Regorafenib.

4 Claims, 8 Drawing Sheets

|  | Subject will be allocated to the following treatment group: | | | |
|---|---|---|---|---|
|  | Regorafenib | | Lomustine | |
|  | N | col % | N | col % |
| pACC | 41 | | 42 | |
| 0= Negative | 15 | 36.6 | 14 | 33.3 |
| 1= Positive | 26 | 53.4 | 28 | 66.7 |

B

| | | Progression-Free Survival | | Overall Survival | |
|---|---|---|---|---|---|
| | | 6-month PFS (95%CI) | p value | 12-month OS (95%CI) | p value |
| pACC | 0= Negative | 13.8 (4.3-28.6) | 0.6577 | 34.5 (18.2-51.4) | 0.4987 |
| | 1=Positive | 9.2 (3.4-18.7) | | 25.9 (15.2-38.0) | |

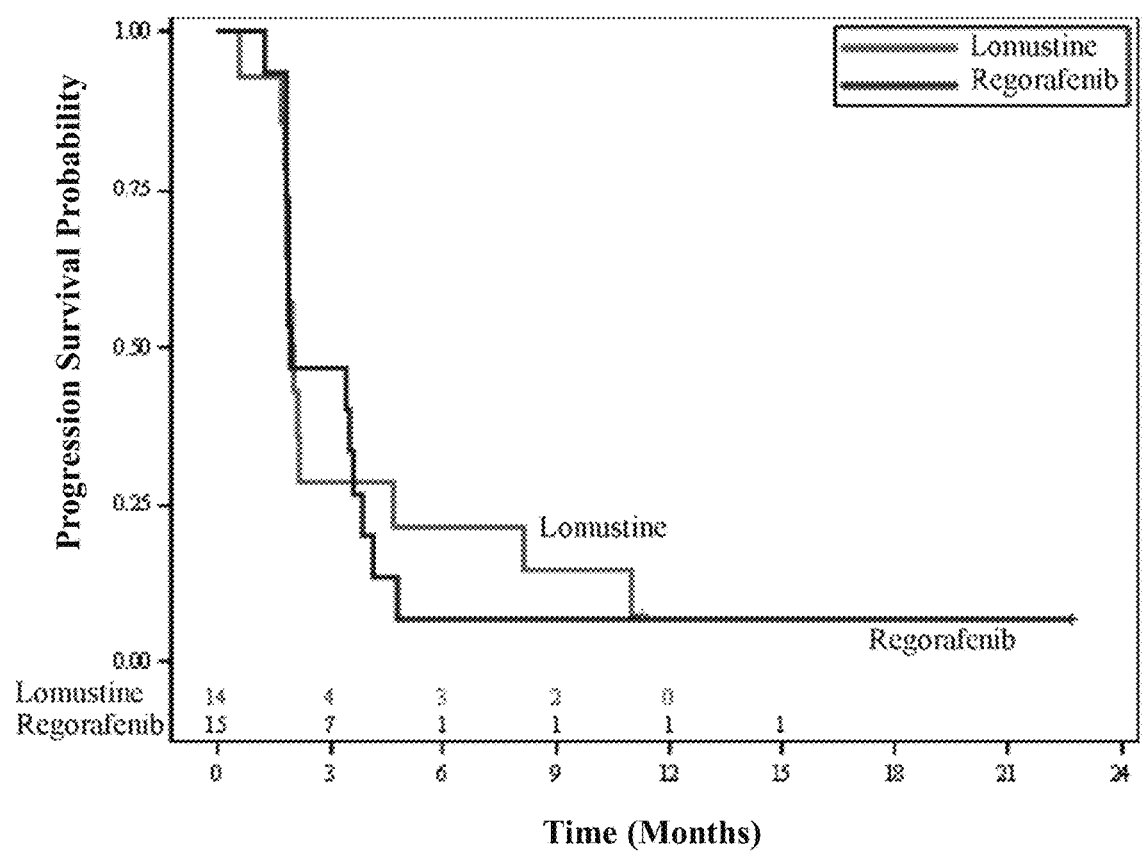

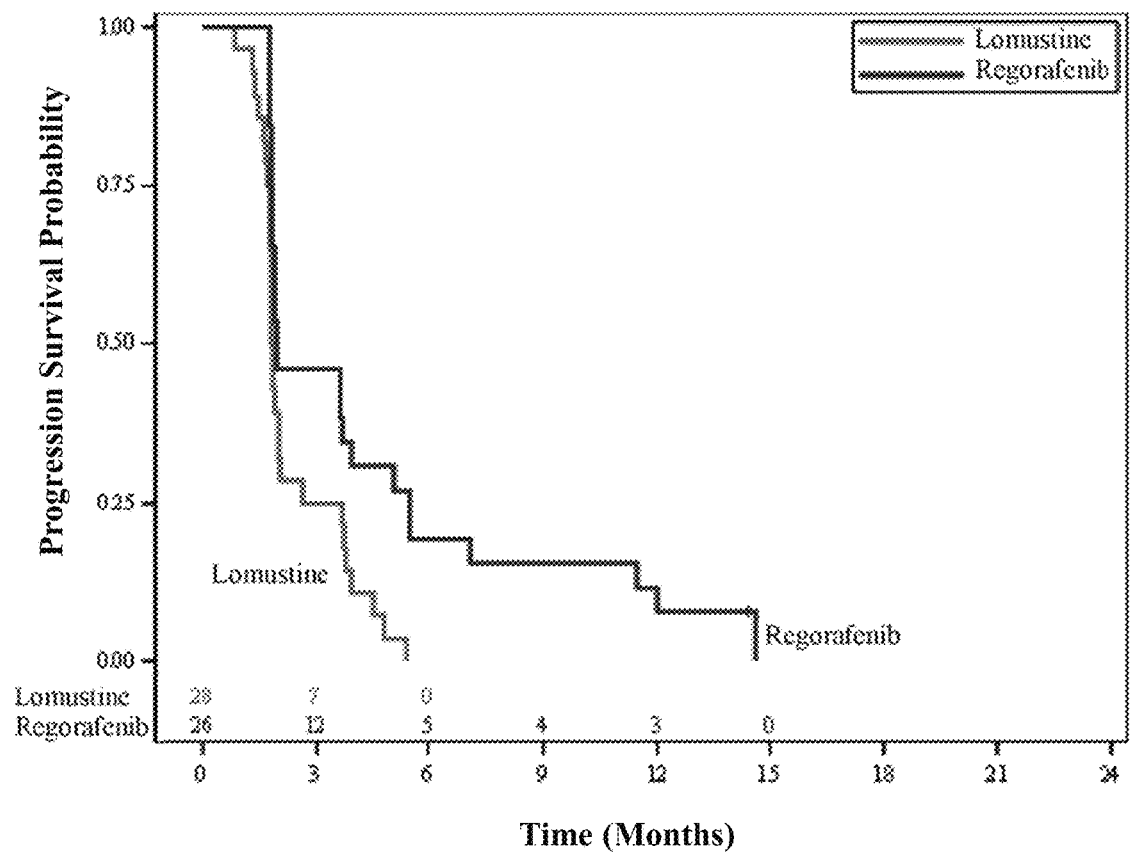

pACC positive (Overall Survival)

Test for interaction p-value = 0.0494

Log Rank test p-value= 0.0015

HR (Reg vs Lom): 0.39 (95%CI: 0.21-0.71);
mOS Rego: 8.0 months (95%CI 5.7-20.5)
mOS Lomu: 5.5 months (95%CI 4.2-7.2)

MARKER FOR IDENTIFYING PATIENTS WITH GLIOBASTOMA WHO RESPOND POSITIVELY TO THE DRUG REGORAFENIB

CROSS-REFERENCE TO RELATED APPLICATIONS

This application is a National Stage Application of International Patent Application No. PCT/IB2019/051991, having an International Filing Date of Mar. 12, 2019, which claims the benefit of priority to Italian Patent Application No. 102018000003449, filed Mar. 12, 2018, the entire contents of which are hereby incorporated by reference herein.

DESCRIPTION

The present invention finds application in the field of medicine, and in particular in the treatment of glioblastoma.

TECHNICAL FIELD OF THE INVENTION

Pharmacological inhibitors of angiogenesis cause indirect effects on tumors associated with the reduction of tumor vasculature, with which an increased hypoxia and reduced availability of nutrients for cancer cells are associated.

It should be noted that although various tumor angiogenesis inhibitors have been developed and sent to clinical trials by the main pharmaceutical companies, these drugs are currently prescribed according to the neoplastic pathology affecting the patient and the stage thereof, and not according to a precise molecular indicator.

Glioblastoma (GBM)

Glioblastoma is a grade IV astrocytoma according to WHO classification and represents the most frequent form (12-15% of cases) of intracranial neoplasms in adults. The standard treatment for glioblastoma is surgery followed by the so-called Stupp protocol, i.e. the concomitant radiotherapeutic and chemotherapeutic treatment with temozolomide (TMZ), followed by a maintenance step with TMZ alone, which increases the average survival at 14.6 months, with a percentage of living patients at 2 years after diagnosis of 26%, and 9.8% at 5 years.

Despite these advances, glioblastoma remains a neoplasm with a fatal prognosis, which invariably recurs with second-line treatment options which are nowadays still very limited.

The guidelines of the European Society of Medical Oncology (ESMO) recommend offering patients with relapsed glioblastoma the opportunity to participate in clinical trials with new drugs and currently there is no second-line chemotherapy having proven efficacy, although some activity has been observed with fotemustine or lomustine in this clinical background.

With regard to treatments with antiangiogenic drugs, glioblastoma is one of the most vascularized tumors and is characterized by the presence of proliferating endothelial cells at histological level.

A pathophysiological feature of glioblastoma is the expression of VEGF and other pro-angiogenic cytokines, stimulating the proliferation, migration, and survival of endothelial blood vessel cells.

The use of angiogenesis inhibitors for the treatment of glioblastoma based on the hypothesis that blocking this process could inhibit tumor growth and prolong patient survival.

Indeed, early studies with VEGF inhibitors, i.e. cediranib and bevacizumab, had provided encouraging data in terms of extension of progression-free survival (PFS) in phase II clinical trials.

Based on these data, the US Food and Drug Administration (FDA) granted accelerated approval of bevacizumab for relapsed glioblastoma in 2009.

However, two phase III randomized clinical trials analyzed bevacizumab activity in association with standard treatment in glioblastoma at diagnosis, and while demonstrating improved PFS and quality of life, no significant survival advantages (OS) emerged.

Resistance to bevacizumab, which selectively inhibits VEGF, could be due, at least in some cases, to the selection of tumor cells capable of producing other pro-angiogenic factors, i.e. bFGF, PlGF, and PDGF.

Regorafenib

Regorafenib potentially affects tumors through various pathways (angiogenesis, oncogenesis, stromagenesis) by inhibiting many receptors having tyrosine kinase (RTK) activity which are active at the level of vasculature (VEGFR1-3, TIE2, FGFR), stroma (PDGF, FGFR) and tumor cells (KIT, RET).

Among the mechanisms inhibited by the drug downstream of these RTKs, the RAS/BRAF pathway can be mentioned, and one of the direct effects, which the drug has in vitro on tumor cells depending on these pathways, is the interruption of cell proliferation and the induction of apoptosis.

The effects on vasculature and stroma are observed in vivo through a reduction of the microvessel density and a slowing down of the tumor growth attributed to the decreased availability of oxygen and nutrients, such as glucose, to support the proliferation of tumor cells. The anti-tumor activity of Regorafenib was demonstrated by many pre-clinical studies.

SUMMARY OF THE INVENTION

The inventors of the present patent application have surprisingly found that tumor samples where the phosphorylated form of serine is expressed in position 79 of the enzyme acetyl-CoA carboxylase ($pACC^{Ser79}$) correspond to patients who have shown a longer survival after the second-line treatment with Regorafenib in a randomized, controlled, phase II clinical trial conducted by Instituto Oncologico Veneto IOV—IRCCS and referred to as REGOMA (EudraCT no.: 2014-003722-41).

OBJECTS OF THE INVENTION

According to a first object, the medical use of the drug Regorafenib is provided for the treatment of glioblastoma in patients who are positive to the marker of the present invention.

According to a second object, a marker for the evaluation of the sensitivity of a patient with glioblastoma to Regorafenib is described.

According to a third object, a method for evaluating the sensitivity of a patient with glioblastoma to Regorafenib is described.

According to a fourth object, a method of treating a patient with glioblastoma comprising the step of evaluating in advance the sensitivity to Regorafenib is described.

According to a fifth object, a diagnostic kit to evaluate the possibility of therapeutic response to Regorafenib in patients with glioblastoma is described.

BRIEF DESCRIPTION OF DRAWINGS

FIG. 4. A: number of patients in the REGOMA study for which the marker pACC$^{Ser79}$ was evaluated; B: analysis of the prognostic value of the marker pACC in the study REGOMA.

DETAILED DESCRIPTION OF THE INVENTION

Figure 1:
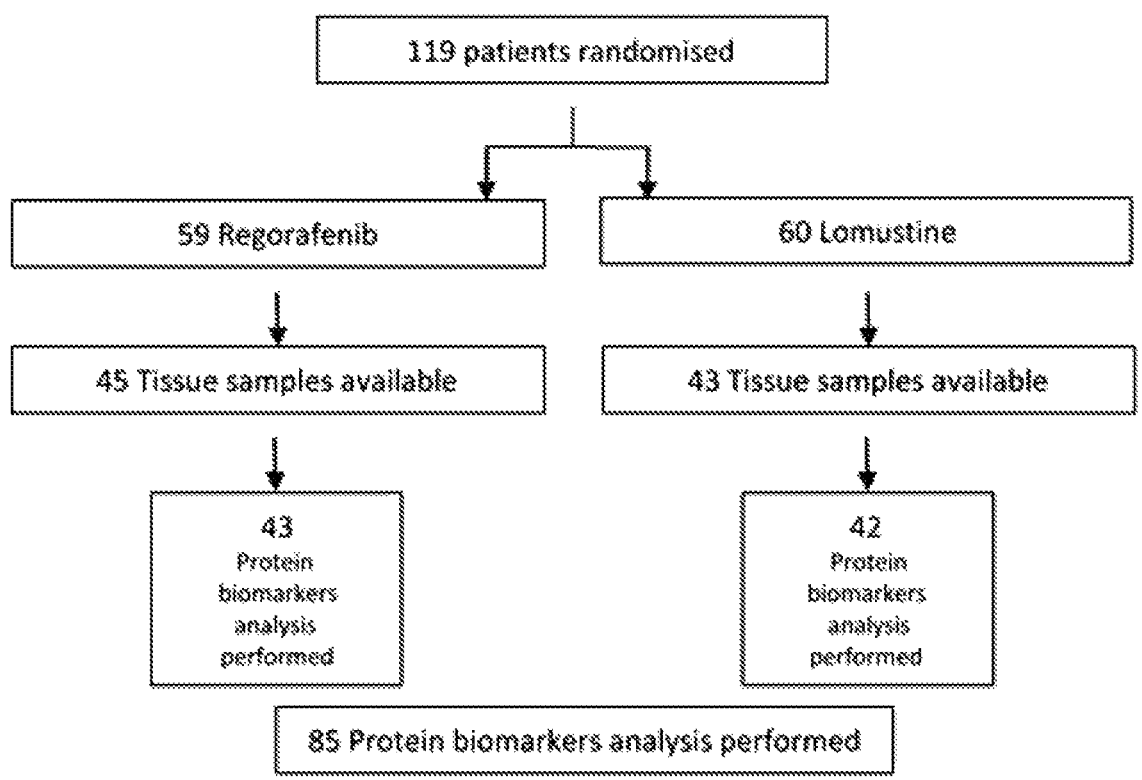
FIG. 1: scheme of the translational study associated with the clinical study REGOMA.
Figure 2:
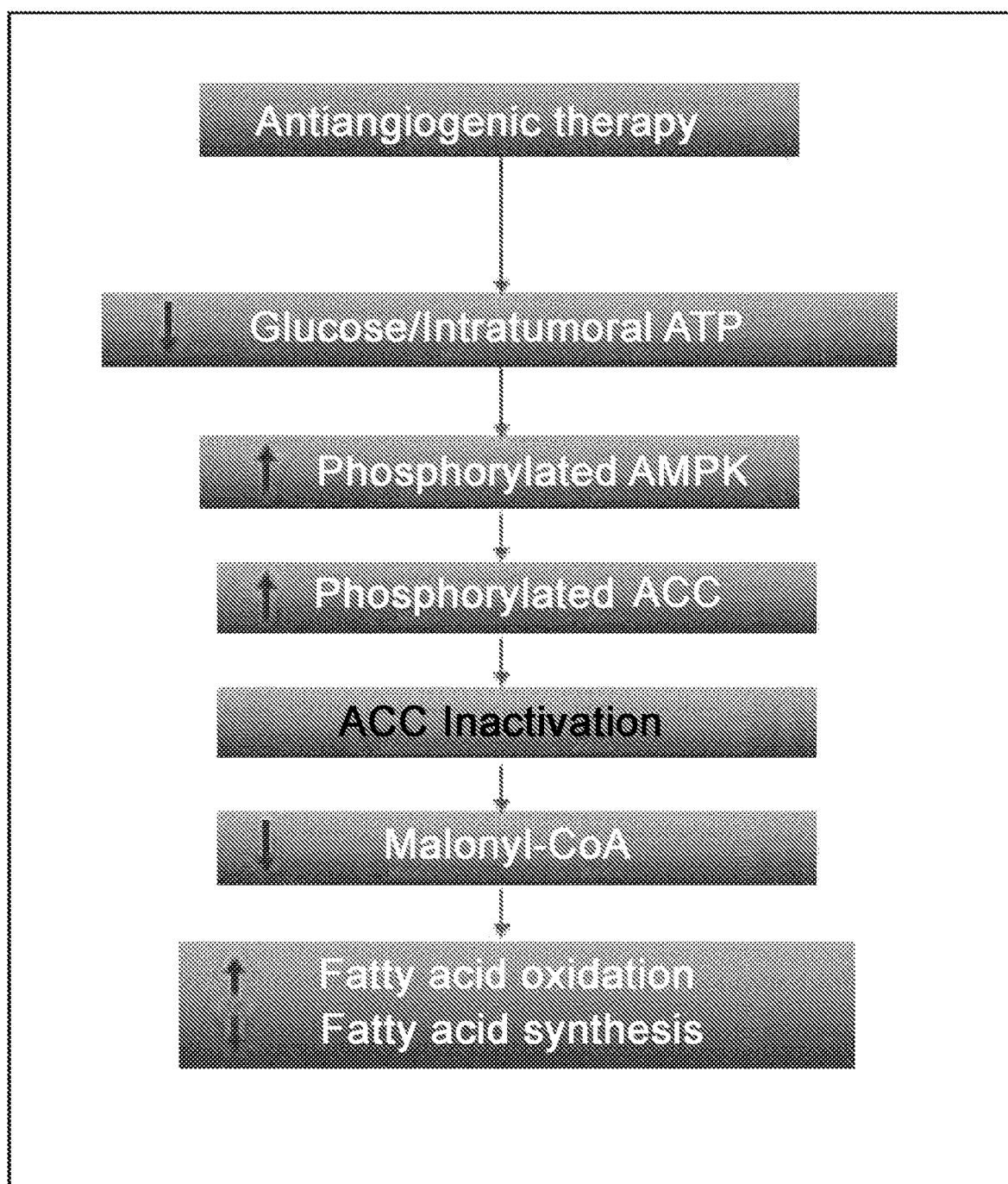
FIG. 2: LKB1/AMPK signaling pathway, which shows how ACC forms part of this pathway, and a phosphorylation target by AMPK. The figure also shows the complex regulation of lipid metabolism by ACC.

According to a first object, the drug Regorafenib is provided for medical use in the treatment of glioblastoma in patients who are positive to the marker of the present invention.

In a preferred aspect, Regorafenib is described for medical use in the context of as a second-line treatment.

A second-line treatment is intended as a treatment performed at the onset of a relapse after performing the first-line treatment of glioblastoma.

In particular, for the purposes of the present invention, the marker-positive patients are patients who are positive to an immunoassay which checks for the presence of a certain marker in tumor cells.

Such a marker is represented by the phosphorylated form of serine at position 79 of the enzyme acetyl-CoA carboxylase (pACC$^{Ser79}$).

More particularly, a patient is defined as positive when said marker is present in at least 5% of the cells in a sample of tumor tissue.

For the evaluation, the whole surface of the sample is taken into account.

The presence of the marker can be at the cytoplasmic or nuclear level.

Positively is evaluated by immunohistochemistry; therefore, the number of stained cells is evaluated.

The results can be read manually or in an automated mode.

If the sample is damaged or has excessive background noise, the sample is defined as not evaluable.

The marker represented by the phosphorylated form of serine in position 79 of the enzyme acetyl-CoA carboxylase (pACC$^{Ser79}$) is per se a further subject of the present invention.

According to a third object, a predictive in vitro method to evaluate the sensitivity of a patient with glioblastoma to treatment with Regorafenib is described.

In particular, such a method comprises the steps of:
providing an isolated sample of a patient's glioblastoma tissue;
evaluating the presence of the marker represented by the phosphorylated form of serine in position 79 of the enzyme acetyl-CoA carboxylase (pACC$^{Ser79}$) in such sample,
wherein the presence of at least 5% of cells wherein said marker is present, at the cytoplasmic or nuclear level, indicates a positive patient, and therefore a sensitivity or a possible sensitivity to the treatment with Regorafenib.

The evaluation of the patient's positively is carried out according to the methods described above.

According to another object, it is described a method for the treatment of glioblastoma comprising a preliminary step of evaluating the patient's sensitivity to Regorafenib.

In a preferred aspect, this method is for the second-line treatment of glioblastoma.

In this regard, a step of determining the presence of a marker represented by the phosphorylated form of serine at position 79 of the enzyme acetyl-CoA carboxylase (pACC$^{Ser79}$) in a sample of tumor tissue of glioblastoma isolated from said patient is carried out, and if said sample is positive, a step of administering Regorafenib to said patient is also carried out.

For the purposes of the present invention, the sample is defined as positive when said marker is present in at least 5% of the cells of said sample.

In particular, the marker may be present at the cytoplasmic or nuclear level.

The percentage of cells in which the marker is present is evaluated manually or in an automated mode, and the percentage of cells in which the marker is present can be evaluated by immunohistochemical methods.

For the purposes of the present invention, in the method for the treatment of the described glioblastoma, Regorafenib is administered to the patient according to the following therapeutic scheme:

| dose x n times/day | daily dose | cycle |
|---|---|---|
| 40 mg x 4 times/day | 160 mg/day | 3 weeks + 1 week break | until the disease progresses or possibly until the toxicity is not acceptable.

According to the fifth object of the present invention, a diagnostic kit to evaluate/predict the possibility of a therapeutic response to Regorafenib in patients with glioblastoma is described.

In particular, such a kit comprises:
an anti-pACC$^{Ser79}$ antibody; and
appropriate immunohistochemistry reagents (IHC), along with the detailed protocol for carrying out and understanding the reaction.

For example, an anti-pACC$^{Ser79}$ antibody which is valid for such a determination is that corresponding to the code #3661 and produced by the company Cell Signaling Technology Inc.

The reagents for IHC are those of the Bond Polymer Refine Detection Kit, Leica, for example.

The invention will be more fully described by the experimental part reported below.

Materials and Methods

In IOV laboratories, studies in experimental mouse models previously showed that anti-angiogenic therapy causes a marked reduction in ATP and glucose levels within tumors, favoring the activation of a particular signaling pathway referred to as LKB1/AMPK. The pathway activation is detected by evaluating the expression in immunohistochemistry (IHC) of the phosphorylated forms of the AMP kinase (AMPK) and acetyl-CoA carboxylase (ACC) markers. Furthermore, in murine models, defects in such a pathway, precluding the phosphorylation of AMPK or ACC, result in early resistance to anti-angiogenic therapy. Such pre-clinical studies have recently been confirmed by the feedback obtained in retrospective clinical trials performed at IOV, which indicated a prognostic role of some markers of the LKB1/AMPK pathway in patients with metastatic colorectal cancer treated with chemotherapy and bevacizumab, and a predictive role of the LKB1 biomarker in patients with advanced lung cancer treated with platinum-based chemotherapy and bevacizumab. Overall, such trials suggested that markers related to tumor cell metabolism, and specifically to the LKB1/AMPK pathway, could have a predictive value in response to anti-angiogenic drugs in cancer patients. On the basis of this hypothesis, it was decided to include some markers such as pAMPK and pACC in the translational part of the REGOMA trial, funded entirely with institutional IOV funds and summarized in FIG. 1.

The recognition of the presence of $pACC^{Ser79}$ in the tumor histological sample is done by immunohistochemistry with a specific anti-pACC antibody (#3661, Cell Signaling Inc.).

The immunohistochemical staining occurred using an automated stainer (LEICA BOND III) provided with its own polymer, which is an indispensable staining system (Bond Polymer Refine Detection). This polymer uses an immunohistochemical staining method based on the use of immune complexes. This method utilizes the normal affinity between antigen and antibody. Three reagents are used: the primary antibody, which is specific for the antigen, the secondary or "bridge" antibody, recognizing the antigens of the primary antibody, and an immunocomplex, which is then recognizable under the microscope, horseradish peroxidase. The primary antibody binds the antigen, the secondary antibody binds the primary antibody while acting as a bridge for the complex consisting of the enzyme peroxidase. The enzyme is then visualized through a substrate-chromogen reaction. The used automated stainer is characterized by the use of secondary antibodies required both for the recognition of mouse and rabbit IgGs linked to the tissue-bound primary antibody, and for the attachment to horseradish peroxidase, thus avoiding the use of the classic streptavidin and biotin method. In fact, the detection system obviates the phenomenon of non-specific staining due to endogenous biotin.

The Bond Polymer Refine Detection is based on the following operating principle:

The removal of paraffin from fixed tissues is carried out by means of a dewaxing solution (Bond Dwax Solution). Washings in absolute alcohol and in a buffer solution for rehydration purposes then follow.

The next step is the unmasking: this step is very important for the re-exposure of antigens masked by the fixation process. In this study, two solutions were used: citrate (pH: 6) and EDTA (pH: 8), following the instructions for each primary antibody. The unmasking time is specific for each antibody.

The sample is incubated for 5 minutes with hydrogen peroxide ($H_2O_2$) to inhibit the endogenous peroxidase activity, thus reducing the risk of non-specific staining.

Application of the specific primary antibody according to its own dilution (15 minutes).

Use of a polymeric IgG HRP (Horse Radish Peroxidase) reagent containing the secondary antibody for the localization of primary rabbit antibodies (8 minutes) which is able to act as a "bridge" between the secondary antibody and the detection system for the chromogen substrate. In this reagent, as well as in the previous one, there is 10% bovine animal serum to saturate the bond with the active sites so as to prevent the binding by the secondary antibody with non-specific sites.

Application of the chromogenic substrate 3,3-diaminobenzidine tetrahydrochloride hydrate (DAB) allowing the visualization of the primary-secondary-antibody-enzyme complex. All this occurs through a reaction between the hydrogen peroxide ($H_2O_2$) which is also able to perform the function of substrate for the enzyme, thus freeing an oxygen atom acting on the existing chromogen, which in turn precipitates generating a brown color (10 minutes).

The last step is the hematoxylin counterstaining which allows the visualization of the cell nuclei.

The use of the Bond Polymer Refine Detection kit reduces the possibility of human error and the variability, which is inherent to the operations.

The evaluation of the sample positively is performed by a skilled operator (biologist or clinician) using an optical microscope, considering the tumor sample as positive if at least 5% of the tumor surface is positive to the marker. Such a percentage is evaluated by digitally acquiring the whole surface of the sample and evaluating the positive area with the Leica Application Suite v3 software.

The stained sample for pACC marker is defined as positive ($pACC^+$) if the staining is present in at least 5% of the tumor cells, negative ($pACC^-$) if less than 5%. Cases in which the sample is damaged or has an excessive background signal are defined as not evaluable (pACC NV).

Figure 3:
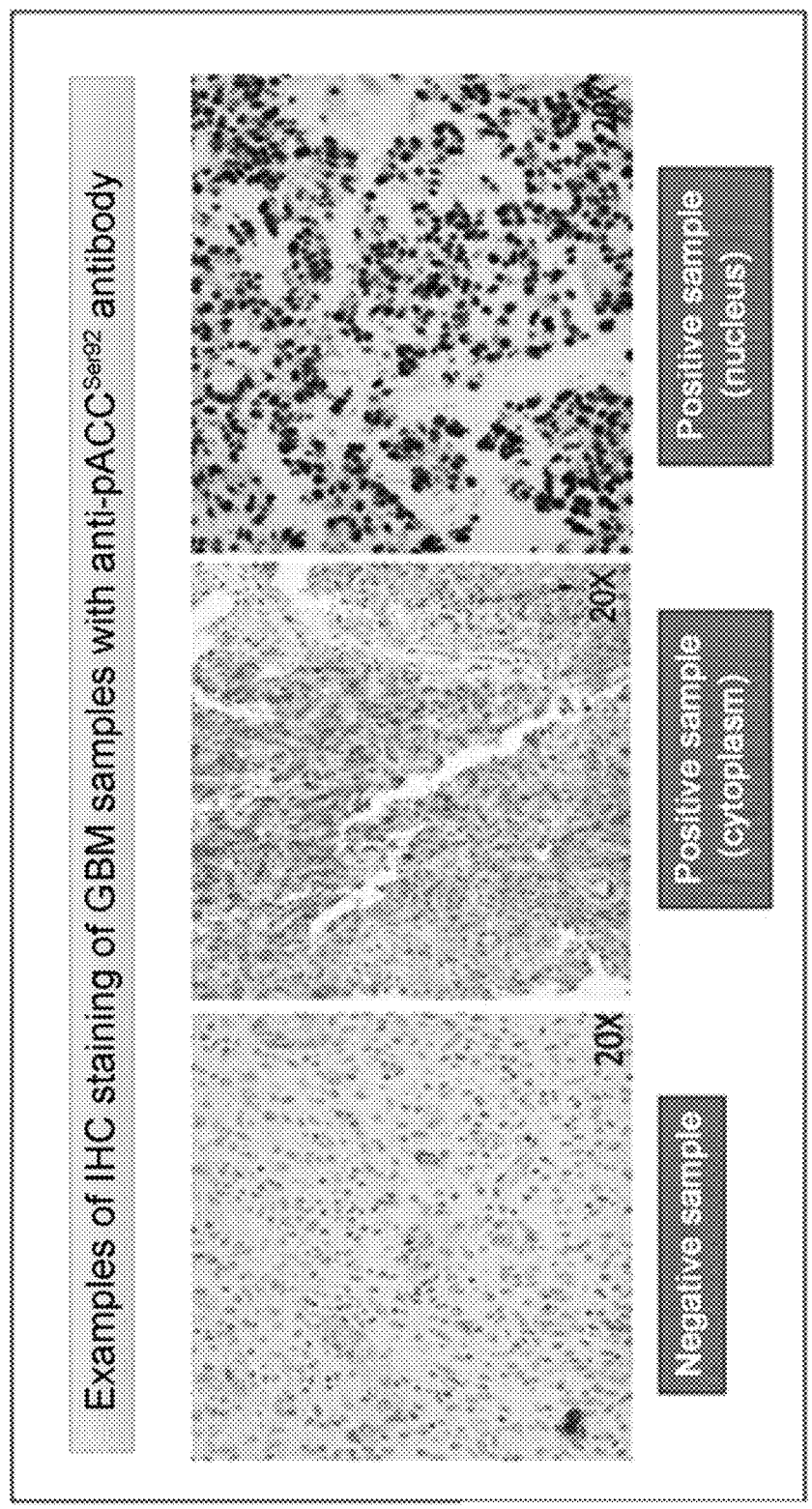
FIG. 3: examples of IHC staining of GBM samples for the marker pACC$^{Ser79}$.

Examples of positive or negative samples for the marker are shown in FIG. 3. The positively for the marker can be cytoplasmic or more rarely nuclear.

Once all samples of the REGOMA trial which are available for the translational study (Table 1) have been stained, the biostatistics and clinical trial team of IOV (Mr. De Salvo—doctor) performed a statistical analysis to evaluate the possible prognostic or predictive meaning of the response of $pACC^{Ser79}$.

To evaluate the prognostic role of $pACC^{Ser79}$, an analysis was carried out according to the Cox model, considering $pACC^{Ser79}$ as an independent variable and dividing the patient samples into positive and negative (as reported above), and survival, being both free from disease progression and as a whole, as a dependent variable.

A value of $p<0.05$ would have been considered statistically significant.

To evaluate the predictive role of $pACC^{Ser79}$, the variable of the treatment received by the patient was added to the Cox model (in particular, according to a randomized assignment, the patient received Regorafenib or Lomustine) in addition to the interaction factor of received treatment*status of the marker $pACC^{Ser79}$ (positive/negative).

A value of $p<0.05$ for the interaction variable would have implied a predictive role of marker response to treatment with Regorafenib.

Figure 5C:
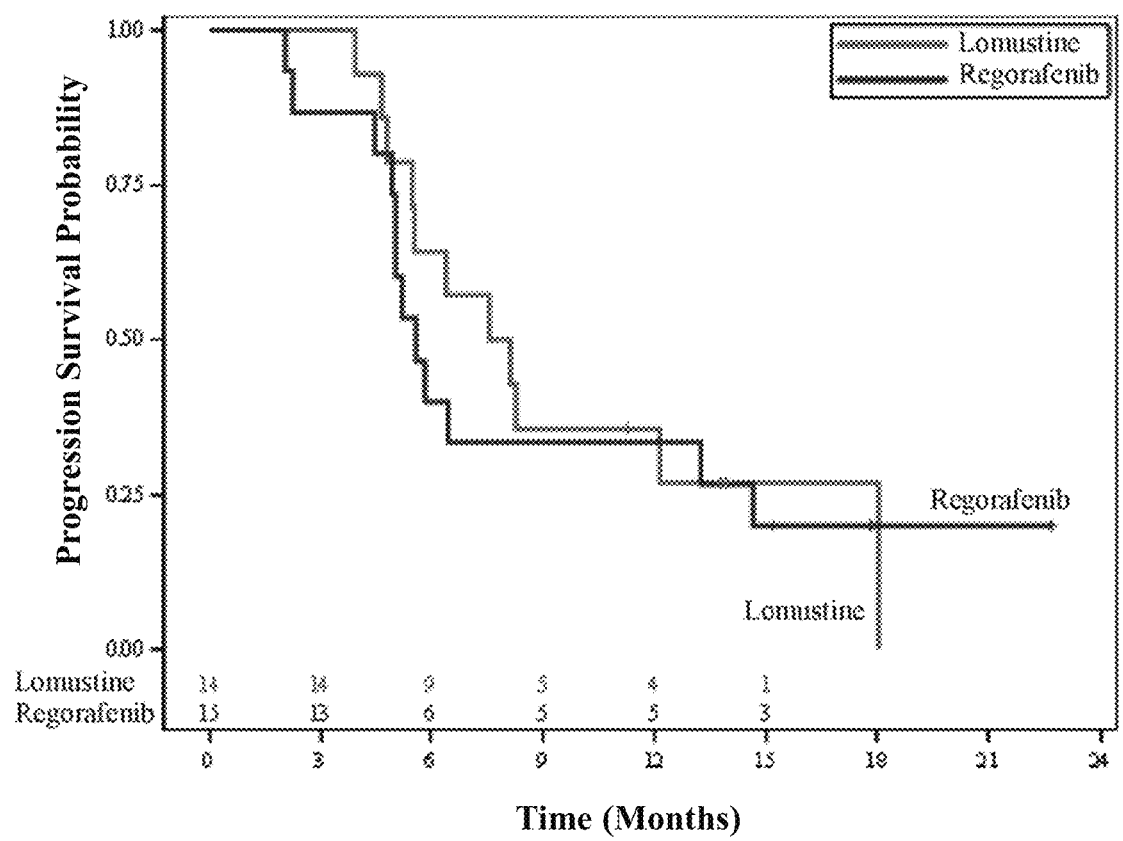
FIG. 5: Analysis of the predictive value of the marker pACC$^{Ser79}$ in the REGOMA study. A-B: effects on PFS and interaction tests. C-D: effects on OS and interaction tests.
Figure 5D:
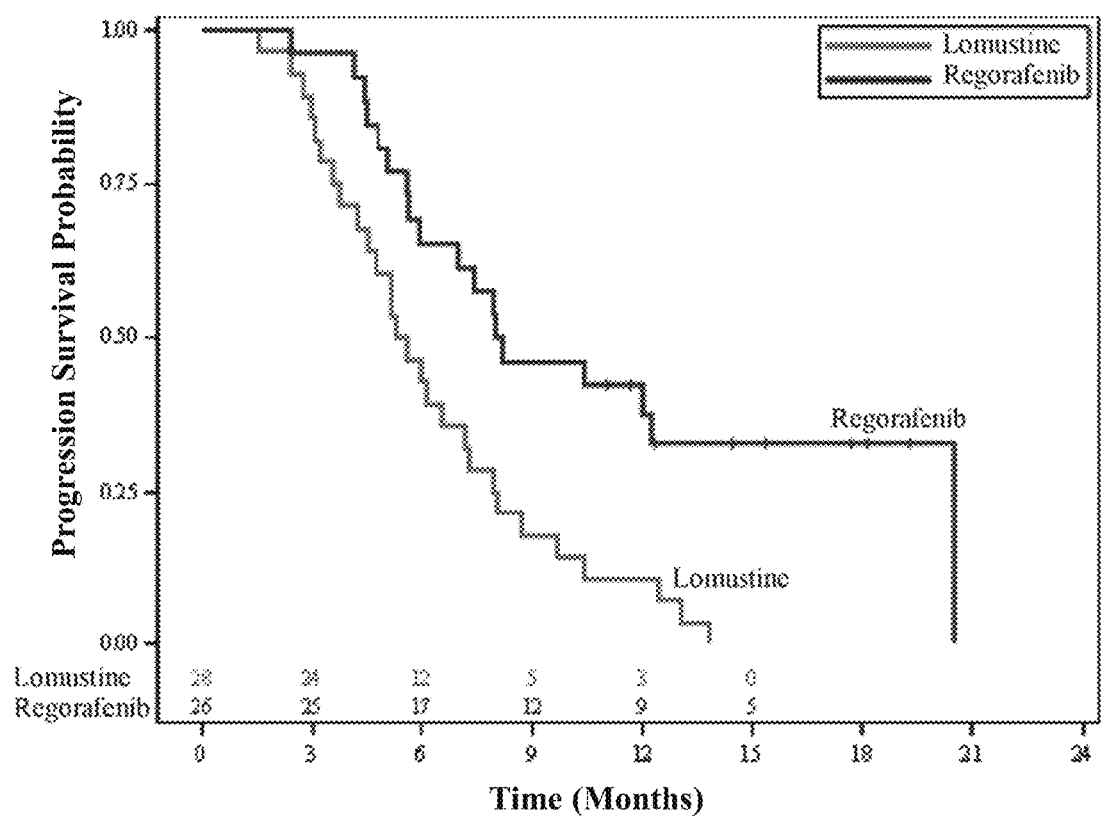

The results of this analysis are shown in FIGS. 4 and 5.

This analysis showed that the positively of the neoplastic tissue to the marker $pACC^{Ser79}$ is able to identify the patients who most benefited from the treatment with Regorafenib, thus taking a predictive significance of response.

The invention claimed is:

1. A method for treating glioblastoma in a patient exhibiting the serine 79-phosphorylated form of the enzyme acetyl-CoA carboxylase (pACCSer79), the method comprising:
    isolating a sample of glioblastoma tumor tissue from said patient;
    determining said sample is positive for a marker represented by the serine 79-phosphorylated form of the enzyme acetyl-CoA carboxylase (pACCSer79); and in response to said determining, administering Regorafenib to said patient to treat said glioblastoma;
wherein said sample is determined to be positive for said marker when pACCSer79 is present in at least 5% of the cells of said sample.

2. The method according to claim 1, wherein said marker may be present at the cytoplasmic or nuclear level.

3. The method according to claim 1, wherein the percentage of cells in which said marker is present is evaluated manually or in an automated mode.

4. The method according to claim 1, wherein the percentage of cells in which said marker is present is evaluated by immunohistochemical methods.

* * * * *